(12) United States Patent
Ozaki et al.

(10) Patent No.: US 11,897,799 B2
(45) Date of Patent: Feb. 13, 2024

(54) MICROORGANISM FOR DEGRADING OILS AND FATS (71) Applicant: CCI HOLDINGS INC., Seki (JP)

(72) Inventors: Koki Ozaki, Seki (JP); Yuta Wakao, Seki (JP)

(73) Assignee: CCI HOLDINGS INC., Seki (JP)

(*) Notice: Subject to any disclaimer, the term of this patent is extended or adjusted under 35 U.S.C. 154(b) by 654 days.

(21) Appl. No.: 17/053,092

(22) PCT Filed: Apr. 12, 2019

(86) PCT No.: PCT/JP2019/016023
§ 371 (c)(1),
(2) Date: Nov. 5, 2020

(87) PCT Pub. No.: WO2019/220831
PCT Pub. Date: Nov. 21, 2019

(65) Prior Publication Data
US 2021/0221721 A1 Jul. 22, 2021

(30) Foreign Application Priority Data
May 17, 2018 (JP) .................. 2018-095351

(51) Int. Cl.
C02F 3/34 (2023.01)
C12N 1/14 (2006.01)
C12R 1/645 (2006.01)

(52) U.S. Cl.
CPC ............. *C02F 3/347* (2013.01); *C02F 3/343* (2013.01); *C12N 1/145* (2021.05); *C12R 2001/645* (2021.05)

(58) Field of Classification Search
CPC ........ C02F 3/344; C02F 3/437; B01D 24/007; B01D 39/04
See application file for complete search history.

(56) References Cited

U.S. PATENT DOCUMENTS 5,156,963 A 10/1992 Eigtved
5,273,898 A 12/1993 Ishii

FOREIGN PATENT DOCUMENTS

| JP | H01501120 A | 4/1989 |
| JP | H03236771 A | 10/1991 |
| JP | 2015192611 A * | 11/2015 |

(Continued)

OTHER PUBLICATIONS

Fell, et. al., Biodiversity and systematics of baidiomycetous yeasts as determined by large subunit rDNA D1/D2 domain sequence, International Journal of Systematic and Evolutionary Microbiology (2000), 50, 1351-1371 (Year: 2000).*

(Continued)

*Primary Examiner* — Bradley R Spies
*Assistant Examiner* — Jeannie McDermott
(74) *Attorney, Agent, or Firm* — BUCHANAN, INGERSOLL & ROONEY PC (57) ABSTRACT Described is a microorganism having an excellent effect of reducing oils and fats, and particularly, *Asterotremella humicola* strain 2-141-1 (Accession No. NITE BP-02641) or a microorganism having the same microbiological properties as those of the foregoing strain. Also described is an effluent treatment method including bringing the microorganism into contact with an effluent including oils and fats.

3 Claims, 1 Drawing Sheet

Specification includes a Sequence Listing.

(56) References Cited

FOREIGN PATENT DOCUMENTS

| JP | 2015192943 A | 11/2015 |
|----|--------------|---------|
| JP | 2017136033 A | 8/2017 |
| JP | 2017177031 A | 10/2017 |
| WO | 88/02775 A1 | 4/1988 |

OTHER PUBLICATIONS

Prillinger, Hansjörg & Lopandic, Ksenija. (2015). Yeast-types of Basidiomycota using cell wall sugars and ribosomal DNA sequences. Stapfia. 103. 3-18. (Year: 2015).*
International Search Report (PCT/ISA/210) and an English translation thereof, and Written Opinion (PCT/ISA/237) dated Jun. 18, 2019, by the Japanese Patent Office as the International Searching Authority for International Application No. PCT/JP2019/016023.
Prillinger et al., "Asterotremella humicola", JCM Catalogue, 1457T-CBS 571, WARP, Apr. 5, 2018, Retrieved from the Internet: URL:http://warp.da.ndl.go.jp/info:ndljp/pid/11066450/www.jcm.riken.jp/cgi-bin/jcm/jcm_number?JCM=1457>.
Prillinger et al., "Asterotremella humicola", JCM Catalogue, 1459-CBS 2041, WARP, Apr. 5, 2018, Retrieved from the Internet: http://warp.da.ndl.go.jp/info:ndljp/pid/11066450/www.jcm.riken.jp/cgi-bin/jcm/jcm_number?JCM=1459>.
Saldanha-Da-Gama, et al., "Characterization of yeasts associated with Portuguese pork-based products", International Journal of Food Microbiology, 1997 (month unknown), vol. 37, pp. 201-207.
Office Action (First Office Action Notification) dated May 9, 2023, by the State Intellectual Property Office of People's Republic of China in corresponding Chinese Patent Application No. 201980032090.3 and an English translation of the Office Action. (18 pages).
Bussamara et al., "Isolation of a Lipase-Secreting Yeast for Enzyme Production in a Pilot-Plant Scale Batch Fermentation", Bioresource Technology, Elsevier, Amsterdam, NL, (Jan. 1, 2010), vol. 101, No. 1, pp. 268-275.
Sitepu et al., "Identification of Oleaginous Yeast Strains Able to Accumulate High Intracellular Lipids when Cultivated in Alkaline Pretreated Corn Stover", Applied Microbiology and Biotechnology, (Sep. 1, 2014), vol. 98, No. 17, pp. 7645-7657.
Witharana et al., "Rapid Degradation of FOG Discharged from Food Industry Wastewater by Lipolytic Fungi as a Bioaugmentation Application", Environmental Technology, (Jul. 11, 2017), vol. 39, No. 16, pp. 2062-2072.
Extended European Search Report dated Feb. 9, 2022, by the European Patent Office in corresponding European Patent Application No. 19802489.5-1111. (8 pages).
Notice of Reasons for Refusal dated Nov. 15, 2022, by the Japanese Patent Office in corresponding Japanese Patent Application No. 2020-519519, and an English translation of the Notice. (8 pages).
Notice of opinion on examination (written notice) dated Jul. 9, 2021, by the Taiwan Intellectual Property Department, Economic Department in corresponding Taiwanese Patent Application No. 108116522, and an English translation of the Notice. (12 pages).

* cited by examiner

MICROORGANISM FOR DEGRADING OILS AND FATS

TECHNICAL FIELD

The present invention relates to a novel microorganism for degrading oils and fats.

BACKGROUND ART

Effluent (wastewater) from kitchens and food factories usually includes kitchen refuse and cooking oil. Solid matter such as kitchen refuse can be easily removed from an effluent by providing a basket trap or the like at the drainage port; however, it is not easy to remove liquid matter such as cooking oil. Therefore, in facilities such as kitchens and food factories, which discharge effluents having large quantities of oils and fats incorporated therein, a pretreatment facility for sewerage (for example, a grease trap) is provided in order to accumulate oils and fats and to separate and dispose of the oils and fats floating in the upper layer.

However, there are occasions in which the oils and fats accumulated inside a grease trap solidify, and the solidified oils and fats remain as scum (oil lumps) on the water surface of the grease trap, or accumulate and adhere to the inner wall surface of the grease trap and the interior of pipes, thereby blocking the pipes. At this time, the accumulated oils and fats may be oxidized and decay, causing offensive odors and pests. Furthermore, when the accumulated oils and fats are left unattended, the ability of the grease trap to remove oils and fats may be reduced, causing the oils and fats to flow out into sewage and rivers. Therefore, when oils and fats are accumulated in the grease trap, it is necessary to ask a specialized contractor to remove the oils and fats by a vacuum treatment, a high-pressure cleaning treatment, and the like, which are all costly.

Thus, with regard to a grease trap, a method of efficiently reducing oils and fats, particularly a method of using microorganisms that perform degradation and assimilation of oils and fats, has been investigated. For example, in Patent Literature 1, *Bacillus subtilis* BN1001 is described as a microorganism that can be used for use applications of reducing n-hexane extractive substances in an oil-containing effluent or degrading the scum collecting in the sump pits in kitchens and the like.

CITATION LIST

Patent Literatures

Patent Literature 1: JP H3-236771 A

SUMMARY OF INVENTION

However, there have been cases in which it is difficult, with conventional microorganisms, to sufficiently reduce the oils and fats included in the effluent of a pretreatment facility for sewerage. Particularly, the water quality such as pH of an effluent in a grease trap can change significantly depending on the food residue to be discharged, or the like. Therefore, microorganisms that are used in grease traps are required to have characteristics of being able to purify effluent even in a water quality environment with a wide range of pH (for example, pH 2.0 or higher and lower than 11.0). However, conventionally known microorganisms do not exhibit such characteristics sufficiently.

Therefore, the present invention was achieved in view of such circumstances, and it is an object of the invention to provide a microorganism having an excellent effect of reducing oils and fats in a pretreatment facility for sewerage. Particularly, an object of the invention is to provide a microorganism capable of purifying an effluent even in a water quality environment with a wide range of pH (for example, pH 2.0 or higher and lower than 11.0).

The inventors of the present invention have conducted intensive studies to solve the above-described problems. As a result, the inventors found that the above-described problems are solved by a microorganism that belongs to *Asterotremella humicola* and exhibits predetermined microbiological properties, and completed the present invention.

DESCRIPTION OF EMBODIMENTS

In the following description, an embodiment according to one aspect of the present invention will be described. The present invention is not intended to be limited only to the following embodiments.

According to the present specification, the expression "X to Y" representing a range means "X or more and Y or less". Furthermore, unless particularly stated otherwise, operations and the measurement of physical properties or the like are carried out under the conditions of room temperature (20° C. to 25° C.) and a relative humidity of 40 to 50% RH.

<Microorganism>

According to one aspect of the present invention, a microorganism that belongs to *Asterotremella humicola* and exhibits the following microbiological properties is provided. The microorganism according to the present invention has an excellent effect of reducing oils and fats in a pretreatment facility for sewerage. Particularly, the microorganism according to the present invention can purify an effluent even in a water quality environment with a wide range of pH (for example, pH 2.0 or higher and lower than 11.0).

TABLE 1-1

| Fermentability test | |
|---|---|
| Glucose | − |
| Assimilability test | |
| Glucose | + |
| Galactose | + |
| L-sorbose | + |
| D-glucosamine | + |
| D-ribose | + |
| D-xylose | + |
| L-arabinose | + |
| D-arabinose | + |
| L-rhamnose | + |
| Sucrose | + |
| Maltose | + |
| Trehalose | + |
| α-methyl-D-glucoside | + |
| Cellobiose | + |
| Salicin | + |
| Melibiose | + |
| Lactose | + |
| Raffinose | D |
| Melezitose | + |
| Inulin | W |

TABLE 1-1-continued

| | |
|---|---|
| Soluble starch | + |
| Glycerol | + |
| Erythritol | + |
| Ribitol | + |
| Xylitol | + |
| D-glucitol | + |
| D-mannitol | + |
| Galactitol | + |
| Inositol | + |
| D-gluconate | + |
| D-glucuronate | + |
| DL-lactate | + |
| Succinate | + |
| Citrate | + |
| Methanol | − |
| Ethanol | + |
| Saccharate | + |
| Nitrate | + |

TABLE 1-2

| Resistance test | |
|---|---|
| Growing at 30° C. | + |
| Growing at 35° C. | W |
| Growing at 37° C. | − |
| 0.01% Cycloheximide | + |
| 50% (w/v) Glucose | + |
| 10% NaCl/5% glucose | − |
| Vitamin auxotrophy test | |
| Vitamin-free medium | D |

"+" Positive
"−" Negative
"W" Weakly positive
"D" Becoming gradually positive over a period of one week or longer after the initiation of test According to a preferred embodiment, the microorganism of the present aspect reduces 1% (w/v) of oils and fats by 50% by weight or more in 24 hours under the conditions of pH 2 or higher and lower than 11.

According to a particularly preferred embodiment, the microorganism of the present aspect is *Asterotremella humicola* strain 2-141-1 (Accession No. NITE BP-02641).

[Screening]

The microorganism according to the present invention was isolated from the soil of Tajimi City, Gifu Prefecture, by the following screening method.

1. Screening Method

An appropriate amount of a sample collected from soil, waste liquid of a grease trap, sewage, river water, hot spring water, or the like in Gifu Prefecture is added to 5 mL of a liquid medium for primary screening prepared by the following method, and the sample is cultured at 30° C. for one week. 100 μL of the culture liquid after culturing is further inoculated into 5 mL of the liquid medium for primary screening, and the sample is cultured again at 30° C. for one week.

The liquid medium for primary screening is prepared by dissolving various components except for oils and fats in pure water so as to obtain the composition shown in the following Table 2, adding oils and fats thereto to obtain a final concentration of 0.5 w/v %, and performing a high temperature and high pressure sterilization. Meanwhile, the oils and fats are prepared by mixing rapeseed oil and soybean oil at a proportion of 1:1 (w/w).

TABLE 2

| Medium component | Final concentration (w/v %) |
|---|---|
| $NH_4Cl$ | 0.05 |
| $K_2HPO_4$ | 0.50 |
| $KH_2PO_4$ | 0.20 |
| $MgSO_4$ | 0.02 |
| NaCl | 0.01 |
| Yeast extract | 0.01 |
| Oils and fats | 0.50 |

(No pH adjustment)

100 μL of the culture liquid after primary screening, which has been diluted $10^4$ times, was applied on an agar medium for secondary screening produced by the following method, and culturing is carried out for hours at 30° C. After culturing, bacterial strains with which the formation of halos caused by degradation of oils and fats could be confirmed are isolated.

The agar medium for secondary screening is prepared by dissolving various components other than oils and fats and agar in pure water so as to obtain the composition shown in the following Table 3, adding oils and fats (rapeseed oil:soybean oil=1:1 (w/w)) to a final concentration of 0.5 w/v % and agar to a final concentration of 2.0 w/v %, performing a high temperature and high pressure sterilization, and then carrying out appropriately dispensing and solidifying.

TABLE 3

| Medium component | Final concentration (w/v %) |
|---|---|
| $NH_4Cl$ | 0.05 |
| $K_2HPO_4$ | 0.50 |
| $KH_2PO_4$ | 0.20 |
| $MgSO_4$ | 0.02 |
| NaCl | 0.01 |
| Yeast extract | 0.01 |
| Oils and fats | 0.50 |
| Tween 80 | 0.20 |
| Agar | 2.00 |

(No pH adjustment)

Next, 0.05 g of oils and fats (rapeseed oil:soybean oil=1:1 (w/w)) is added to 5 mL of a liquid medium for tertiary screening produced by the following method, and thereby a sterilized test liquid is prepared (oils and fats 1% (w/v)). Each of the isolated bacterial strains obtained by the above-described secondary screening is inoculated using a platinum loop into an LB medium produced by the following method, in an amount of one platinum loop at a time, and shaking culture (140 rpm) is carried out for 24 hours at 30° C. 100 μL of the culture liquid thus obtained is inoculated into the test liquid prepared by the above-described method, and shaking culture (140 rpm) is carried out for 24 hours at 30° C.

The liquid medium for tertiary screening is prepared by dissolving various components in pure water so as to obtain the composition shown in the following Table 4, adjusting the solution to pH 6.0 with hydrochloric acid, and performing a high temperature and high pressure sterilization.

TABLE 4

| Medium component | Final concentration (w/v %) |
|---|---|
| KCl | 0.0021 |
| NaCl | 0.0045 |
| $MgSO_4$ | 0.0027 |
| $CaCl_2$ | 0.0031 |

TABLE 4-continued

| Medium component | Final concentration (w/v %) |
|---|---|
| Fish meat extract | 0.1200 |
| Tryptone | 0.1800 |

The LB medium is prepared by dissolving various components purely so as to obtain the composition shown in the following Table 5, and performing a high temperature and high pressure sterilization.

TABLE 5

| Medium component | Final concentration (w/v %) |
|---|---|
| Tryptone | 1.00 |
| Yeast extract | 0.50 |
| NaCl | 1.00 |

After culturing, a normal-hexane extract is prepared according to the revised version of JIS K0102:2016 (Testing methods for industrial wastewater). The normal-hexane extract is designated as a residual amount of oils and fats, and from 0.05 g of the oils and fats added at the time of preparing the test liquid and the residual amount of oils and fats (amount (g) of the normal-hexane extract), the oils and fats reduction rate is determined by the following Mathematical Formula (1). As a result, a bacterial strain having a high oils and fats reduction rate can be isolated.

[Mathematical Formula 1]

Mathematical Formula (1)

$$\text{Oils and fats reduction rate (wt\%)} = \frac{\text{Added oils and fats }(g) - \text{residual amount of oils and fats }(g)}{\text{Added oils and fats }(g)} \times 100$$

For the isolated bacterial strain having a high oils and fats reduction rate, the base sequence in the 26S rDNA-D1/D2 region was determined. The determined base sequence of the 26S rDNA-D1/D2 region of the isolated microorganism is set forth in SEQ ID NO: 1 described below.

[Chemical Formula 1]
(base sequence of 26S rDNA-D1/D2 region)
SEQ ID NO: 1
A A A C T A A C A A G G A T T C C C C T A G T A G

C G G C G A G T G A A G C G G G A A G A G C T C A

A A T T T G T A A T C T G G C G T C T T T C A G G

C G T C C G A G T T G T A A T C T A T A G A A G T

G T T T T C C G T G C T G G A C C A T G T C C A A

G T C C C T T G G A A C A G G G T A T C A A A G A

G G G T G A C A A T C C C G T A C T T G A C A T G

A C C A C C A G T G C T C T G T G A T A C A C T T

T C T A C G A G T C G A G T T G T T T G G G A A T

G C A G C T C A A A A T G G G T G G T A A A T T C

C A T C T A A A G C T A A A T A T T G G C G A G A

G A C C G A T A G C G A A C A A G T A C C G T G A

G G G A A A G A T G A A A A G C A C T T T G G A A

A G A G A G T T A A A C A G T A C G T G A A A T T

G T T G A A A G G G A A A C G A T T G A A G T C A

G T C G T G T T C A T T G G A C T C A G C C G G T

T T T C G G T G T A T T T C C T T T G A A G G G G

T C A A C A T C A G T T T T G T C C G G T G G A T

A A A G G C A G G A A G A A A G T G G C T C C C T

C G G G A G T G T T A T A G C T T T C T G T C A C

A T A C A C T G G A G G A G A C T G A G G A C T G

C A G C T C G C C T T T T G G G G G G G G T T C G

C C C A C G T T C G A G C T T A G G A T G T T G A

C A T A A T G G C T T T A A A C G A C

As a result of a BLAST search in a DNA database for identifying microorganisms, DB-FU10.0 (TechnoSuruga Laboratory Co., Ltd.) and an international base sequence database (DDBJ/ENA(EMBL)/GenBank), the base sequence of the 26S rDNA-D1/D2 region of the isolated microorganism showed high homology (homology ratio: 99.3 to 100%) with the base sequence of the 26S rDNA-D1/D2 region of the genus *Asterotremella*. The isolated microorganism showed high homology with a homology ratio of 100% particularly with respect to *Asterotremella humicola* (current name: *Vanrija humicola*) strain CBS571 (Accession No. AF189836). Thus, the isolated microorganism was presumed to belong to *Asterotremella humicola*.

2. Chemical Properties

The microbiological properties of the bacterial strain obtained by the above-described screening will be described below. The following was used for morphological observation.

TABLE 5

| Microscope | Optical microscope BX51 (manufactured by Olympus Corporation) (including differential interference observation) Stereoscopic microscope SMZ800 (manufactured by NIKON CORPORATION) |
|---|---|
| Mounting liquid | Sterilized distilled water |

Furthermore, as a medium, YM agar plate medium (1.0% (w/v) glucose, 0.5% (w/v) peptone, a 0.3% (w/v) malt extract, a 0.3% (w/v) yeast extract, and 1.5% (w/v) agar) (no pH adjustment) was used.

2-1. Colony Observation

During one week of aerobic culture on the YM agar plate medium at 27° C., colonies exhibited the following properties.

TABLE 6

| | |
|---|---|
| Shape of margin | Entire |
| Elevation state | Flat to pulvinate |
| Surface shape | Smooth to slightly rough |
| Gloss and nature | Buttery, moist |
| Color tone | White to cream color |

2-2. Morphological Observation

In the first week after the initiation of culture at 27° C. on the YM agar plate medium, it was confirmed that vegetative cells had an elliptical shape or a club shape, and proliferation was achieved by budding.

On the YM agar plate medium at 27° C., formation of a sexual organ was not recognized on the plate after a lapse of 2 months of culture.

2-3. Physiological Properties Tests

The methods for the test for physiological properties were carried out according to Kurtzman, C. P., Fell, J. W. and Boekhout, T. (2011) The Yeasts, a taxonomic study, 5th Edition. Elsevier, Amsterdam, Netherlands, and culturing was carried out at 25° C., except for a temperature resistance test. The results are presented in Tables 7-1 and 7-2. Furthermore, in addition to the isolated bacterial strain obtained as described above, known physiological properties of *A. humicola*, to which the isolated bacterial strain is presumed to belong, will be described together.

TABLE 7-1

| | Isolated bacterial strain | Known *A. humicola* | |
|---|---|---|---|
| | | CBS571[Ta)] | The Yeasts 5[th b)] |
| Fermentability test | | | |
| Glucose | − | − | − |
| Assimilability test | | | |
| Glucose | + | + | + |
| Galactose | + | + | + |
| L-sorbose | + | + | + |
| D-glucosamine | + | W | + |
| D-ribose | + | + | + |
| D-xylose | + | + | + |
| L-arabinose | + | − | +/S |
| D-arabinose | + | + | + |
| L-rhamnose | + | + | + |
| Sucrose | + | + | + |
| Maltose | + | + | + |
| Trehalose | + | + | + |
| α-methyl-D-glucoside | + | + | + |
| Cellobiose | + | + | + |
| Salicin | + | − | + |
| Melibiose | + | W | + |
| Lactose | + | + | + |
| Raffinose | D | W | −/S |
| Melezitose | + | + | + |
| Inulin | W | − | −/W |
| Soluble starch | + | − | − |
| Glycerol | + | + | +/S |
| Erythritol | + | + | + |
| Ribitol | + | + | + |
| Xylitol | + | + | + |
| D-glucitol | + | + | + |
| D-mannitol | + | + | + |
| Galactitol | + | W | + |
| Inositol | + | W | + |
| D-gluconate | + | + | + |
| D-glucuronate | + | + | + |
| DL-lactate | + | − | + |
| Succinate | + | W | + |
| Citrate | + | − | + |
| Methanol | − | − | − |
| Ethanol | + | − | + |

TABLE 7-1-continued

| | Isolated bacterial strain | Known *A. humicola* | |
|---|---|---|---|
| | | CBS571[Ta)] | The Yeasts 5[th b)] |
| Saccharate | + | W | + |
| Nitrate | + | − | − |

TABLE 7-2

| Resistance test | | | |
|---|---|---|---|
| Growing at 30° C. | + | + | + |
| Growing at 35° C. | W | + | V |
| Growing at 37° C. | − | − | − |
| 0.01% Cycloheximide | + | + | ND |
| 50% (w/v) Glucose | + | − | − |
| 10% NaCl/5% glucose | − | − | − |
| Vitamin auxotrophy test | | | |
| Vitamin-free medium | D | ND | − |

"+" Positive
"−" Negative
"W" Weakly positive
"D" Becoming gradually positive over a period of one week or longer after the initiation of test
"S" Becoming gradually positive over a period of 2 to 3 weeks or longer after the initiation of test
"V" Variation depending on strains is recognized
"ND" Data was not described
a) Cited from CBS strain database
b) Cited from The Yeasts, a taxonomic study, 5th ed. (Kurtzman et al., 2011)

3. Various Properties

The isolated bacterial strain had properties different from those of conventionally known yeast that belongs to *Asterotremella humicola*, in terms of the assimilability of soluble starch and nitrates, viability in 50% glucose, and the like. Therefore, the isolated bacterial strain was considered as a novel microorganism, and this bacterial strain was named as *Asterotremella humicola* strain 2-141-1 (hereinafter, also simply referred to as "strain 2-141-1"). Furthermore, this strain 2-141-1 was deposited with an international depositary authority, National Institute of Technology and Evaluation Patent Microorganisms Depositary (NPMD) (2-5-8 Kazusakamatari, Room No. 122, Kisarazu City, Chiba Prefecture, 292-0818, Japan) on Feb. 21, 2018, and the Accession Number of the strain is NITE BP-02641.

Strain 2-141-1 belongs to *Asterotremella humicola* and reduces 1% (w/v) oils and fats by 50% by weight or more in 24 hours under the conditions of pH 2.0 or higher and lower than 11.0, and preferably pH 2.0 or higher and 10.5 or lower. Furthermore, the strain 2-141-1 reduces 1% (w/v) oils and fats by 50% by weight or more in 24 hours under the conditions of 30° C. and pH 2.0 or higher and lower than 11.0, and preferably pH 2.0 or higher and 10.5 or lower. The lower limit of the pH is more preferably 2.5 or higher. Further, the upper limit of the pH is more preferably 10.0 or lower, and even more preferably 9.0 or lower.

[Evaluation of Oils and Fats Reducing Effect]

According to the present specification, the reduction of oils and fats is evaluated by the following method. That is, a test liquid is prepared (oils and fats 1% (w/v)) by adding 0.05 g of oils and fats, which include rapeseed oil:soybean oil=1:1 (w/w), to a sterilization-treated medium for evaluating oils and fats degradation (5 mL), the medium being the same as the above-described liquid medium for tertiary screening except for the pH. As the medium for evaluating oils and fats degradation used at this time, a medium having the pH adjusted to the range of 1.5 to 11.0 is used (for example, a medium for evaluating oils and fats degradation at pH 1.5, 2, 2.5, 3, 4, 5, 6, 7, 8, 9, 10, 10.5, and 11). The adjustment of pH may be carried out using any arbitrary acids including an inorganic acid such as hydrochloric acid, nitric acid, carbonic acid, or sulfuric acid, and an organic acid such as citric acid or lactic acid, and salts thereof; and/or any arbitrary alkalis such as sodium hydroxide, potassium hydroxide, and ammonia; hydrochloric acid (acidic side) or sodium hydroxide (alkali side) is preferable.

The microorganism cultured on a plate medium (for example, the agar medium for secondary screening) is inoculated into this test liquid, and the microorganism is subjected to shaking (140 rpm) culture for 24 hours at any arbitrary temperature. The amount of the bacterium to be inoculated is about one platinum loop taken with a platinum loop. Regarding the microorganism to be inoculated into the test liquid, a microorganism that has been precultured in an LB medium or the like may be used. By performing pre-culture, the amount of bacterium to be inoculated can be easily regulated. In the case of using a precultured microorganism, the microorganism is inoculated to a concentration of $1.5 \times 10^6$ CFU/mL with respect to 1 mL of the test liquid. The culturing temperature may be set in accordance with a temperature range in which the capacity of bacterial cells for degrading and assimilating oils and fats is high; the culturing temperature is, for example, 15 to 35° C., and preferably 20 to 30° C.

After culturing, a normal-hexane extract is prepared according to the revised version of JIS K0102:2016 (Testing methods for industrial wastewater). The normal-hexane extract is designated as a residual amount of oils and fats, and from the oils and fats (0.05 g) added at the time of preparing the test liquid and the residual amount of oils and fats (amount (g) of the normal-hexane extract), the oils and fats reduction rate is determined by the above-described Mathematical Formula (1). The microorganism according to the present invention may be such that the oils and fats reduction rate that is determined by the above-described method is 50% by weight or more with respect to the entirety of the test liquid prepared using a medium for evaluating oils and fats degradation, in which the pH has been set to the above-described range (for example, pH 2.0 to 10.5). According to a preferred embodiment of the present invention, the oils and fats reduction rate in the case of culturing at 30° C. is 50% by weight or more, and more preferably 90% by weight or more. Since it is more preferable as the oils and fats reduction rate is higher, the upper limit is not particularly limited; for example, the oils and fats reduction rate to be measured by the above-described method is 90% or less. When culturing is carried out for a long time period, the oils and fats reduction amount becomes large. However, since the microorganism is sequentially excreted from the pretreatment facility for sewerage, the microorganism is usually supplemented to the pretreatment facility for sewerage every 1 to 3 days. Therefore, the microorganism exhibiting an oils and fats reduction rate of 50% by weight or more in a short period of time (for example, within 24 hours) is excellent in terms of practical use.

The water quality environment for an effluent from a pretreatment facility for sewerage can easily fluctuate depending on the type of the kitchen refuse discharged, or the like. Therefore, it is preferable that the microorganism that is used in the pretreatment facility for sewerage is capable of purifying an effluent in an environment with a wide range of pH. Strain 2-141-1 is superior from the viewpoint of being capable of degrading oils and fats even in an environment with a wide range of pH (for example, pH 2.0 to 10.5).

The term "oils and fats" according to the present specification refers to edible or industrial oils and fats including large quantities of glycerides such as triglycerides, diglycerides, and monoglycerides, and fatty acids. Examples of the oils and fats include edible oils and fats such as olive oil, canola oil, coconut oil, sesame oil, rice oil, rice bran oil, safflower oil, soybean oil, corn oil, rapeseed oil, palm oil, palm kernel oil, sunflower oil, cotton seed oil, palm oil, peanut oil, beef tallow, lard, chicken oil, fish oil, whale oil, butter, margarine, fat spread, and shortening; and industrial oils and fats such as linseed oil, Jatropha oil, tall oil, hamana oil, castor oil, and jojoba oil. Preferred are edible oils and fats that are frequently discharged from restaurants and the like, where grease traps are installed in many cases. Fatty acids are not particularly limited; examples include saturated fatty acids such as butyric acid, hexanoic acid, heptanoic acid, octanoic acid, decanoic acid, lauric acid, tridecanoic acid, myristic acid, pentadecanoic acid, pentadecanoic acid, palmitic acid, heptadecanoic acid, stearic acid, arachidic acid, behenic acid, and lignoceric acid; and unsaturated fatty acids such as decenoic acid, myristoleic acid, pentadecenoic acid, palmitoleic acid, heptadecenoic acid, oleic acid, eicosenoic acid, docosenoic acid, tetracosenoic acid, hexadecadienoic acid, hexadecatrienoic acid, hexadecatetraenoic acid, linoleic acid, α-linolenic acid, γ-linolenic acid, octadecatetraenoic acid, eicosadienoic acid, eicosatrienoic acid, eicosatetraenoic acid, arachidonic acid, eicosapentaenoic acid, henicosapentaenoic acid, docosadienoic acid, docosatetraenoic acid, docosapentaenoic acid, docosapentaenoic acid, and docosahexaenoic acid. The fatty acids may be products produced as edible or industrial oils and fats are degraded.

[Culturing of Microorganism]

A method for culturing the microorganism belonging to *Asterotremella humicola* (hereinafter, also simply referred to as "microorganism for degrading oils and fats") according to the present invention may be any method as long as the microorganism can grow and proliferate by the method. For example, the medium used for culturing the microorganism may be any of a solid medium or a liquid medium, and any of a synthetic medium or a natural medium may be used as long as it is a medium containing a carbon source that can be assimilated by the microorganism used, and appropriate amounts of a nitrogen source, an inorganic salt, and other nutrients. Usually, the medium includes a carbon source, a nitrogen source, and inorganic substances.

The carbon source that can be used for the culture of a microorganism for degrading oils and fats is not particularly limited as long as it is a carbon source that the bacterial strain to be used can assimilate. Specific examples include, in consideration of the assimilability of the microorganism, sugars such as glucose, fructose, cellobiose, raffinose, xylose, maltose, galactose, sorbose, glucosamine, ribose, arabinose, rhamnose, sucrose, trehalose, α-methyl-D-glucoside, salicin, melibiose, lactose, melezitose, inulin, erythritol, ribitol, xylitol, glucitol, mannitol, galactitol, inositol, N-acetyl-D-glucosamine, starch, a starch hydrolysate, molasses, and blackstrap molasses; natural products such as barley and rice; alcohols such as glycerol, methanol, and ethanol; organic acids such as acetic acid, lactic acid, succinic acid, gluconic acid, glucuronic acid, pyruvic acid, and citric acid; hydrocarbons such as hexadecane; and the like. The above-described carbon sources are appropriately selected by taking the assimilability by the microorganism to be cultured into consideration. For example, in the case of using strain 2-141-1, among the above-described carbon sources, it is preferable to use glucose, galactose, sorbose, glucosamine, arabinose, rhamnose, sucrose, maltose, trehalose, α-methyl-D-glucoside, cellobiose, salicin, melibiose, lactose, melezitose, a starch hydrolysate, glycerol, erythritol, ribitol, xylitol, glucitol, mannitol, galactitol, inositol, gluconic acid, glucuronic acid, lactic acid, succinic acid, citric acid, gluconic acid, ethanol, and the like. Furthermore, one kind or two or more kinds of the above-described carbon sources can be selected and used.

Examples of the nitrogen source that can be used for the culture of the microorganism for degrading oils and fats include organic nitrogen sources such as a meat extract, a fish meat extract, peptone, polypeptone, tryptone, a yeast extract, a malt extract, a soybean hydrolysate, a soybean powder, casein, milk casein, casamino acid, various amino acids containing glycine, glutamic acid, and aspartic acid, corn steep liquor, and hydrolysates of other animals, plants, microorganisms, and the like; inorganic nitrogen sources such as ammonia, ammonium salts containing ammonium nitrate, ammonium sulfate, and ammonium chloride, nitrates containing sodium nitrate, nitrites containing sodium nitrite, and urea; and the like. The above-described nitrogen sources are appropriately selected by taking the assimilability by the microorganism to be cultured into consideration. For example, in the case of using strain 2-141-1, among the above-described nitrogen sources, it is preferable to use a fish meat extract, tryptone, a yeast extract, ammonium chloride, and the like.

Furthermore, one kind or two or more kinds of the above-described nitrogen sources can be selected and used.

Examples of an inorganic substance that can be used for the culture of the microorganism for degrading oils and fats include phosphates, hydrochlorides, sulfates, acetates, carbonates, and halides such as chlorides, of magnesium, manganese, calcium, sodium, potassium, copper, iron, zinc, and the like. The above-described inorganic substances are appropriately selected by taking the assimilability by the microorganism to be cultured into consideration. Furthermore, one kind or two or more kinds of the above-described inorganic substances can be selected and used. If necessary, a surfactant and the like may also be added into the medium.

In order to cause the microorganism according to the present invention to efficiently degrade and assimilate oils and fats, or to maintain the capacity of the microorganism for degrading and assimilating oils and fats, it is preferable to add oils and fats into the medium. Examples of the oils and fats include the above-mentioned edible oils and fats, industrial oils and fats, and fatty acids. The amount of addition of oils and fats is not particularly limited and can be appropriately selected by taking the capacity for degrading and assimilating oils and fats by the microorganism to be cultured, and the like. Specifically, it is preferable to add oils and fats (rapeseed oil:soybean oil=1:1 (w/w)) at a concentration of 1 to 30 g, and more preferably 5 to 15 g, in 1 L of the medium. With such an amount of addition, the microorganism can maintain high capacity for degrading and assimilating oils and fats. Meanwhile, oils and fats may be added singly or may be added in the form of a mixture of two or more kinds thereof.

Culturing of the microorganism according to the present invention can be carried out by a conventional method. For example, depending on the type of the microorganism, the microorganism is cultured under aerobic conditions or anaerobic conditions. In the case of the former, culture of the microorganism is carried out by shaking, ventilation stirring, or the like. Furthermore, the microorganism may be cultured continuously or in batches. The culturing conditions are appropriately selected according to the composition of the medium and the culturing method, and the culturing conditions are not particularly limited as long as they are conditions in which the microorganism according to the present invention can proliferate, and can be appropriately selected according to the type of the microorganism to be cultured. Usually, the culturing temperature is preferably 15 to 40° C., and more preferably 25 to 35° C. Furthermore, the pH of the medium adequate for culturing is not particularly limited; however, the pH is preferably 2 to 10.5, and more preferably 2.5 to 9.0. Moreover, the culturing time is not particularly limited and varies depending on the type of the microorganism to be cultured, the amount of the medium, the culturing conditions, and the like. Usually, the culturing time is preferably 16 to 48 hours, and more preferably 20 to 30 hours.

<Effluent Treatment Method>

An embodiment of the present invention relates to an effluent treatment method including a step of bringing an effluent including oils and fats into contact with the microorganism according to the present invention as described above. The microorganism according to the present invention has an excellent effect of reducing oils and fats, and particularly, the microorganism has a characteristic that can purify an effluent even in a water quality environment with a wide range of pH (for example, pH 2 or higher and lower than 11.0). Therefore, oils and fats can be effectively reduced by bringing an effluent including oils and fats into contact with the microorganism according to the present invention as described above. A preferred embodiment of the present invention is an effluent treatment method of incorporating *Asterotremella humicola* strain 2-141-1 into an effluent including oils and fats. Meanwhile, the description on the above-described microorganism can be modified and applied to the present embodiment, as necessary.

In the following description, the effluent treatment method according to the present aspect will be described in more detail with reference to FIG. 1. Meanwhile, the effluent treatment method of the present invention is not intended to be limited to FIG. 1.

Figure 1:
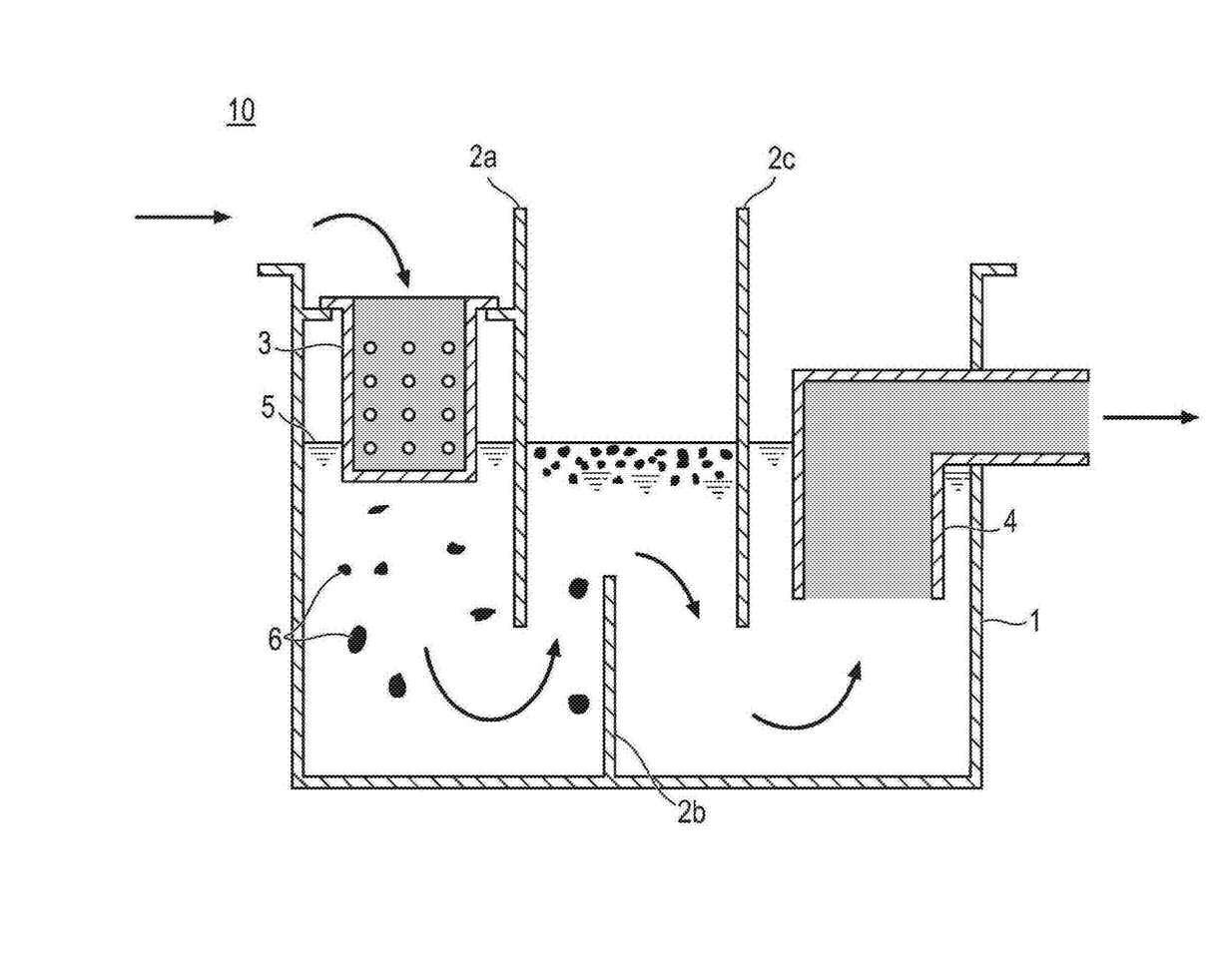
FIG. 1 schematically illustrates the mechanism of an effluent treatment by a grease trap.

FIG. 1 schematically illustrates the mechanism of an effluent treatment (wastewater treatment) by a grease trap 10. In the effluent treatment method, the microorganism according to the present invention may be added in advance to an effluent before being discharged into the grease trap 10; typically, the microorganism is added to an effluent in an effluent treatment tank 1. However, the effluent treatment method according to the present invention is not particularly limited so long as the method is capable of bringing the microorganism according to the present invention into contact with an effluent containing oils and fats.

The grease trap 10 may be an embedded type, a movable type, or the like, and the form of installation is not particularly limited. In the case of an embedded type, for example, in a kitchen or a food processing plant, the grease trap 10 is embedded such that an effluent that has flowed out into a drainage ditch is poured into a residue receptacle 3. In the case of a movable type, for example, the grease trap 10 is installed such that a residue receptacle 3 is positioned in the lower part of a drain gutter of a sink.

In FIG. 1, the effluent flows in the direction of the arrow. Meanwhile, throwing of the effluent into the grease trap 10 may be carried out batchwise or continuously. An effluent containing oils and fats flows toward an effluent treatment tank 1 through a residue receptacle 3. At this time, all or some of residue such as kitchen refuse is collected at the residue receptacle 3; however, most of oils and fats pass through the residue receptacle 3 and flow into the effluent treatment tank 1. The oils and fats 6 that have flowed into the effluent treatment tank 1 float toward the water surface 5 by means of a partition version 2b and accumulate in a space partitioned by partition plates 2a and 2c. Therefore, when the microorganism according to the present invention is not added to the effluent, oils and fats 6 gradually agglomerate in the space partitioned by the partition plates 2a and 2c and form scum.

When the microorganism according to the present invention is applied to the grease trap 10, the effluent including oils and fats is brought into contact with the microorganism according to the present invention in the effluent treatment tank 1 (mainly in the space partitioned by the partition plates 2a and 2c). Since the microorganism according to the present invention has high oils and fats degradation activity and has assimilability, the microorganism can suppress agglomeration of the oils and fats 6 and can effectively prevent the formation of scum. Particularly, strain 2-141-1 comprises high degradation activity for oils and fats also in a wide range of pH regions (for example, pH 2.0 or higher and lower than 11.0). Thereby, oils and fats are prevented from flowing out to an external environment through a trapping pipe 4 independently of the pH of the effluent, and there is an advantage even from the viewpoint of environmental protection.

With regard to the effluent treatment method, the microorganism according to the present invention can be brought into contact with effluent in various forms, such as a state of being suspended in the culture liquid, a state of being collected as a solid fraction from the culture liquid, a state of being dried, and a state of being immobilized on a carrier. The microorganism in a state of being suspended in the culture liquid and collected as a solid fraction from the culture liquid, or in a state of being dried is, for example, added into an effluent and is brought into contact with the effluent. The microorganism in a state of being immobilized on a carrier may be added into the effluent; the microorganism and the effluent can also be brought into contact with each other by installing a carrier having the microorganism immobilized thereon in a grease trap and passing the effluent through the microorganism-immobilized carrier. By installing the microorganism immobilized on a carrier in a grease trap, the microorganism can be prevented from flowing out together with the effluent and causing a decrease in the number of bacterial cells.

In the case of using the microorganism according to the present invention that has been collected as a solid fraction from the culture liquid, regarding the collecting method, any means that is known to a person skilled in the art can be employed. For example, the microorganism can be obtained by subjecting a culture liquid of a microorganism for degrading oils and fats, which has been cultured by the above-mentioned method, to solid-liquid separation by centrifugal separation, filtration, or the like, and collecting a solid fraction. When this solid fraction is dried (for example, freeze-dried), a microorganism for degrading oils and fats in a dried state can be obtained.

In the case of using a microorganism for degrading oils and fats in a state of being immobilized on a carrier, the carrier for immobilizing the microorganism for degrading oils and fats is not particularly limited as long as the carrier can have the microorganism immobilized thereon, and any carrier that is generally used for immobilizing a microorganism is used in the same manner or after being appropriately modified. For example, a method of entrapping the microorganism in a gel-like material such as alginic acid, polyvinyl alcohol, gellan gum, agarose, cellulose, and dextran; a method of adsorbing and immobilizing the microorganism on the surface of glass, activated carbon, polystyrene, polyethylene, polypropylene, wood, silica gel, or the like; and the like can be used.

Furthermore, the method of immobilizing the microorganism for degrading oils and fats on a carrier is also not particularly limited, and a general method for immobilizing a microorganism is used in the same manner or with modification. For example, an immobilization method involving pouring a culture liquid of a microorganism into a carrier, an immobilization method involving placing a carrier under reduced pressure using an aspirator and pouring a culture liquid of a microorganism into a carrier, a method of pouring a culture liquid of a microorganism into a sterilized mixture of a medium and a carrier, performing shaking culture, and naturally drying the carrier taken out from the mixture, and the like, may be mentioned.

With regard to the method according to the present invention, in a case in which the microorganism for degrading oils and fats is added and brought into contact with an effluent, the amount of the bacterium to be added can be arbitrarily set. The amount of the bacterium to be added to an effluent is not particularly limited; the amount is, for example, $1 \times 10^4$ to $1 \times 10^{12}$ CFU, and preferably $1 \times 10^5$ to $1 \times 10^{11}$ CFU, with respect to 1 g of the oils and fats included in the effluent. Alternatively, for example, the amount is 0.1 mg to 5 g (weight of dried bacterial cells), preferably 1 mg to 1.5 g (weight of dried bacterial cells), and more preferably 10 mg to 150 mg (weight of dried bacterial cells), with respect to 1 g of the oils and fats included in the effluent. Alternatively, the amount may also be, for example, an amount that gives $1 \times 10^6$ to $1 \times 10^{12}$ CFU/L, and more preferably $1 \times 10^7$ to $1 \times 10^{11}$ CFU/L, with respect to the effluent inside the grease trap. Alternatively, the amount is, for example, 10 mg to 15 g (weight of dried bacterial cells)/L, and preferably 0.1 g to 1.5 g (weight of dried bacterial cells)/L, with respect to the effluent inside the grease trap. In the case of using two or more kinds of microorganisms in combination, the amount means the total amount. Meanwhile, regarding the microorganism to be added to the effluent, a precultured microorganism may be used. By performing preculture, the amount of bacterium to be inoculated can be easily regulated.

When an effluent is discharged to an external environment, the microorganism for degrading oils and fats, which is not immobilized on a carrier, is discharged out of the grease trap together with the effluent. Therefore, in the present invention, it is preferable to regularly add the microorganism for degrading oils and fats to the grease trap. The interval of addition is not particularly limited; it is preferable to add the microorganism at an interval of, for example, once/3 hours, once/24 hours, or once in 2 to 3 days. The method of adding is not particularly limited, and in a case in which effluent flows in continuously to the grease trap, the microorganism may be added in a state of being incorporated into the effluent, or may be added directly to the effluent inside the grease trap. When the microorganism is added through a drainage port of a sink of the kitchen or the like, the microorganism can be introduced into the grease trap together with the effluent that is discharged due to washing.

With regard to the effluent treatment method, from the viewpoint of reducing oils and fats more efficiently, other components may also be added to the effluent in addition to the microorganism according to the present invention. Examples of the other components include the microorganism described in JP 2017-136033 A, a lipase, a pH adjusting agent, a oils and fats adsorbent, a surfactant, and the like.

The grease trap may have a form of having an effluent containing oils and fats continuously introduced thereinto and continuously discharging the effluent after treatment, or may have a form of having an effluent containing oils and fats introduced thereinto, treating the effluent in a lump, and then discharging in a lump the effluent after treatment.

Furthermore, with regard to the effluent treatment method according to the present invention, the temperature at the time of bringing the microorganism for degrading oils and fats into contact with oils and fats, that is, the temperature of the effluent inside the grease trap, can be arbitrarily set. Also, the pH at the time of bringing the microorganism for degrading oils and fats into contact with oils and fats, that is, the pH of the effluent inside the grease trap, can also be arbitrarily set. Generally, the temperature is, for example, 10 to 50° C., preferably 15 to 35° C., and more preferably 20 to 30° C. The pH is, for example, 2.0 or higher and lower than 11.0, preferably 2.0 to 10.5, and more preferably 2.5 to 9.0. Furthermore, if necessary, the effluent may be subjected to aeration by aerating or the like.

<Effluent Treating Agent>

According to an embodiment of the present invention, an effluent treating agent including the above-described microorganism according to the present invention is provided. The microorganism according to the present invention has an excellent effect of reducing oils and fats and particularly has characteristics that can purify an effluent even in a water quality environment with a wide range of pH (for example, pH 2.0 or higher and lower than 11.0). Therefore, oils and fats can be effectively reduced by using an effluent treating agent including the microorganism according to the present invention for an effluent treatment facility (pretreatment facility for sewerage) such as a grease trap. The description on the microorganism and the effluent treatment method can be modified, as necessary, and applied to the present embodiment.

The effluent treating agent may be either in a dry form or liquid; a dry form such as a powder, granules, a pellet, or a tablet is preferred from the viewpoint of preservability. The microorganism according to the present invention that is used for the effluent treating agent in such a dry form may be in the form of a bacterial cell powder obtained by drying a culture liquid by spray-drying, freeze-drying, or the like, or bacterial cells in a state of being immobilized on a carrier as described above, and the microorganism may also be formed into a powder, granules, a pellet, or a tablet. Alternatively, the bacterial cells or the culture liquid may also be encapsulated using hydroxypropyl methyl cellulose, gelatin, or the like. The effluent treating agent may also include an excipient such as hydroxypropyl cellulose, dextrin, lactose, or starch.

The microorganism according to the present invention included in the effluent treating agent may be a killed bacterium or a live bacterium; from the viewpoint of the sustainability of the degradation activity for oils and fats, it is preferable that the microorganism is a live bacterium.

The amount of the microorganism according to the present invention that is included in the effluent treating agent is, for example, 10 to 100% by weight in, for example, the solid content of the effluent treating agent. Alternatively, the amount of the microorganism according to the present invention that is included in the effluent treating agent is, for example, an amount that gives $1 \times 10^2$ to $1 \times 10^{10}$ CFU/g with respect to the entirety of the effluent treating agent. Furthermore, as long as the intended effects of the present invention are achieved, the effluent treating agent may also include, for example, one or more kinds of additives selected from the group consisting of another microorganism that can live symbiotically with the above-described microorganism according to the present invention, a lipolytic enzyme, a oils and fats adsorbent, and a surfactant. As the other microorganism that can live symbiotically, the lipolytic enzyme, the oils and fats adsorbent, and the surfactant, for example, those described in JP 2017-136033 A can be used.

EXAMPLES

The effects of present invention will be described using the following Examples and Comparative Examples. However, the technical scope of the present invention is not intended to be limited only to the following Examples.

Example 1: Isolation of Microorganism

A sample collected from the soil of Tajimi City, Gifu Prefecture, was inoculated into a liquid medium for primary screening by the above-described method and cultured for one week at 30° C. 100 μL of the culture liquid after culturing was further inoculated into 5 mL of a liquid medium for primary screening and was cultured again for one week at 30° C.

100 μL of the culture liquid after primary screening, which had been diluted $10^4$ times, was applied on an agar medium for secondary screening produced by the above-described method, and culturing was carried out for one week at 30° C. After culturing, bacterial strains for which the formation of halos caused by degradation of oils and fats could be recognized were isolated.

Next, 0.05 g of oils and fats (rapeseed oil:soybean oil=1:1 (w/w)) were added to 5 mL of a liquid medium for tertiary screening produced by the above-described method, and thereby a sterilized test liquid was prepared (oils and fats 1% (w/v)). Each of the isolated bacterial strains obtained by the above-described secondary screening was inoculated using a platinum loop into an LB medium produced by the above-described method, in an amount of one platinum loop at a time, and the bacterial strains were subjected to shaking culture (140 rpm) for 24 hours at 30° C. 100 μL of the culture liquid thus obtained was inoculated into the test liquid prepared by the above-described method and was subjected to shaking culture (140 rpm) for 24 hours at 30° C.

After culturing, a normal-hexane extract was prepared according to the revised version of JIS K0102:2016 (Testing methods for industrial wastewater). The normal-hexane extract was designated as a residual amount of oils and fats, and from 0.05 g of the oils and fats added at the time of preparing the test liquid and the residual amount of oils and fats (amount (g) of the normal-hexane extract), the oils and fats reduction rate was determined by the following Mathematical Formula (1). As a result, a bacterial strain having a high oils and fats reduction rate was isolated.

[Mathematical Formula 2]

$$\text{Oils and fats reduction rate (wt\%)} = \frac{\text{Added oils and fats }(g) - \text{residual amount of oils and fats}(g)}{\text{Added oils and fats}(g)} \times 100 \qquad \text{Mathematical Formula (1)}$$

The isolated bacterial strain was named as *Asterotremella humicola* strain 2-141-1 and was deposited with National Institute of Technology and Evaluation Patent Microorganisms Depositary (Accession No. NITE BP-02641).

Example 2: Evaluation of Oils and Fats Reduction Rate 0.05 g of oils and fats were added to 5 mL of a liquid medium for tertiary screening, whose pH had been adjusted to the range of 1.5 to 11.0 using hydrochloric acid or sodium hydroxide, and thereby a sterilized test liquid was prepared. The isolated bacterial strain cultured on an agar medium for secondary screening was inoculated with a platinum loop into the test liquid prepared as described above, in an amount of one platinum loop, and the bacterial strain was subjected to shaking culture (140 rpm) for 24 hours at 30° C.

Furthermore, as an object of comparison, 0.75 mg of "Grease Guard (registered trademark) D Lipase" (Novozymes A/S) or 7.5 mg of "BN-CLEAN (powder)" (Meiji Food Material Co., Ltd.; including *Bacillus subtilis* BN1001) was added to the test liquid prepared as described above, and the mixture was subjected to shaking for 24 hours at 30° C.

After culturing, a normal-hexane extract was prepared according to the revised version of JIS K0102:2016 (Testing methods for industrial wastewater). The normal-hexane extract was designated as a residual amount of oils and fats, and from 0.05 g of the oils and fats added at the time of preparing the test liquid and the residual amount of oils and fats (amount (g) of the normal-hexane extract), the oils and fats reduction rate was determined by the above-described Mathematical Formula (1). Results thereof are presented in the following Table 8. In Table 8, the value of the oils and fats reduction rate is presented as an average value (n=3).

TABLE 8

| | Oils and fats reduction rate (wt %) pH | | | | | | | | | | | | |
|---|---|---|---|---|---|---|---|---|---|---|---|---|---|
| | 1.5 | 2.0 | 2.5 | 3.0 | 4.0 | 5.0 | 6.0 | 7.0 | 8.0 | 9.0 | 10.0 | 10.5 | 11.0 |
| A. humicola strain 2-141-1 | −1.0 | 51.2 | 94.2 | 95.9 | 92.4 | 95.2 | 96.3 | 97.9 | 94.5 | 93.9 | 67.2 | 54.2 | 14.5 |
| Grease Guard ™ D Lipase | −1.2 | 0.5 | 0.2 | 1.2 | 0.3 | 20.4 | 24.3 | 27.2 | 24.9 | 22.1 | 14.9 | 10.2 | 4.3 |
| BN-CLEAN | 0.5 | −0.3 | 0.4 | 0.6 | 0.2 | 1.2 | 1.4 | 2.3 | 5.4 | 1.4 | 0.6 | 1.3 | −1.2 |

As shown in Table 8, it is understood that strain 2-141-1 reduced 1% (w/v) oils and fats by 50% by weight or more in 24 hours under the conditions of 30° C. and pH 2.0 or higher and lower than 11.0. That is, it is understood that strain 2-141-1 has excellent oils and fats degradation ability even in a water quality environment with a wide range of pH.

The present patent application is based on Japanese Patent Application No. 2018-095351 filed on May 17, 2018, the disclosure of which is incorporated in its entirety by reference.

REFERENCE SIGNS LIST

1 EFFLUENT TREATMENT TANK
2a, 2b, 2c PARTITION PLATE
3 RESIDUE RECEPTACLE
4 TRAPPING PIPE
5 WATER SURFACE
6 OILS AND FATS
10 GREASE TRAP

---

The invention claimed is:

1. An effluent treatment method, comprising bringing *Asterotremella humicola* strain 2-141-1 (Accession No. NITE BP-02641) into contact with an effluent including oils and fats.

2. The effluent treatment method according to claim 1, wherein *Asterotremella humicola* strain 2-141-1 (Accession No. NITE BP-02641) exhibits the following microbiological properties:

| Fermentability test | |
| --- | --- |
| Glucose | − |
| Assimilability test | |
| Glucose | + |
| Galactose | + |
| L-sorbose | + |
| D-glucosamine | + |
| D-ribose | + |
| D-xylose | + |
| L-arabinose | + |
| D-arabinose | + |
| L-rhamnose | + |
| Sucrose | + |
| Maltose | + |
| Trehalose | + |
| α-methyl-D-glucoside | + |
| Cellobiose | + |
| Salicin | + |
| Melibiose | + |
| Lactose | + |
| Raffinose | D |
| Melezitose | + |
| Inulin | W |
| Soluble starch | + |
| Glycerol | + |
| Erythritol | + |
| Ribitol | + |
| Xylitol | + |
| D-glucitol | + |
| D-mannitol | + |
| Galactitol | + |
| Inositol | + |
| D-gluconate | + |
| D-glucuronate | + |
| DL-lactate | + |
| Succinate | + |
| Citrate | + |
| Methanol | − |
| Ethanol | + |
| Saccharate | + |
| Nitrate | + |
| Resistance test | |
| Growing at 30° C. | + |
| Growing at 35° C. | W |
| Growing at 37° C. | − |
| 0.01% Cycloheximide | + |
| 50% (w/v) Glucose | + |
| 10% NaCl/5% glucose | − |
| Vitamin auxotrophy test | |
| Vitamin-free medium | D |

"+" Positive
"−" Negative
"W" Weakly positive
"D" Becoming gradually positive over a period of one week or longer after the initiation of test.

3. The effluent treatment method according to claim 1, wherein *Asterotremella humicola* strain 2-141-1 (Accession No. NITE BP-02641) reduces 1% (w/v) oils and fats by 50% by weight or more in 24 hours under conditions of pH 2 or higher and lower than 11.

* * * * *

SEQUENCE LISTING

<160> NUMBER OF SEQ ID NOS: 1

<210> SEQ ID NO 1

<211> LENGTH: 594
<212> TYPE: DNA
<213> ORGANISM: Asterotremella humicola

<400> SEQUENCE: 1

```
aaactaacaa ggattcccct agtagcggcg agtgaagcgg gaagagctca aatttgtaat      60
ctggcgtctt tcaggcgtcc gagttgtaat ctatagaagt gttttccgtg ctggaccatg     120
tccaagtccc ttggaacagg gtatcaaaga gggtgacaat cccgtacttg acatgaccac     180
cagtgctctg tgatacactt tctacgagtc gagttgtttg ggaatgcagc tcaaaatggg     240
tggtaaattc catctaaagc taatatattgg cgagagaccg atagcgaaca agtaccgtga    300
gggaaagatg aaaagcactt tggaaagaga gttaaacagt acgtgaaatt gttgaaaggg     360
aaacgattga agtcagtcgt gttcattgga ctcagccggt tttcggtgta tttcctttga    420
acgggtcaac atcagtttg tccggtggat aaaggcagga agaaagtggc tccctcggga    480
gtgttatagc tttctgtcac atacactgga ggagactgag gactgcagct cgccttttgg    540
ccggggttcg cccacgttcg agcttaggat gttgacataa tggctttaaa cgac           594
```